(12) United States Patent
Miller (10) Patent No.: US 9,931,108 B2
(45) Date of Patent: Apr. 3, 2018

(54) SYSTEM AND METHOD FOR INFLUENCING AN ANATOMICAL STRUCTURE

(76) Inventor: Steven Miller, Boynton Beach, FL (US)

(*) Notice: Subject to any disclaimer, the term of this patent is extended or adjusted under 35 U.S.C. 154(b) by 2026 days.

(21) Appl. No.: 11/610,332

(22) Filed: Dec. 13, 2006

(65) Prior Publication Data

US 2007/0118097 A1 May 24, 2007

Related U.S. Application Data (63) Continuation-in-part of application No. 11/283,104, filed on Nov. 18, 2005, now Pat. No. 7,621,908.

(51) Int. Cl.
*A61B 17/00* (2006.01)
*A61B 17/02* (2006.01)

(52) U.S. Cl.
CPC .... *A61B 17/0218* (2013.01); *A61B 2017/003* (2013.01)

(58) Field of Classification Search
USPC ............................................. 600/141; 606/1
See application file for complete search history.

(56) References Cited

U.S. PATENT DOCUMENTS

| | | | |
|---|---|---|---|
| 4,581,017 A | 4/1986 | Sahota | |
| 5,087,244 A | 2/1992 | Wolinsky et al. | |
| 5,588,961 A | 12/1996 | Leone et al. | |
| 5,651,769 A | 7/1997 | Waxman et al. | |
| 6,067,990 A | 5/2000 | Kieturakis | |
| 6,148,222 A | 11/2000 | Ramsey, III | |
| 6,159,146 A | 12/2000 | El Gazayerli | |
| 6,497,704 B2 | 12/2002 | Ein-Gal | |
| 6,582,388 B1 | 6/2003 | Coleman et al. | |
| 6,913,604 B2 | 7/2005 | Mihalik et al. | |
| 7,047,074 B2 | 5/2006 | Connelly et al. | |
| 7,052,493 B2 | 5/2006 | Vaska et al. | |
| 7,089,063 B2 | 8/2006 | Lesh et al. | |
| 7,041,095 B2 | 9/2006 | Wang et al. | |
| 7,678,117 B2 * | 3/2010 | Hinman et al. | ............... 606/108 |
| 8,529,443 B2 | 9/2013 | Maloney | |
| 2004/0138700 A1* | 7/2004 | Cooper et al. | ............... 606/205 |
| 2007/0118105 A1 | 5/2007 | Miller | |

* cited by examiner

*Primary Examiner* — Aaron Roane
(74) *Attorney, Agent, or Firm* — McHale & Slavin, P.A.

(57) ABSTRACT

A relocation system for influencing an anatomical structure in relation to an internal surgical site. The system is composed of an elongated member constructed and arranged for insertion into a patient. The elongated member is composed of a plurality of segments interconnected by a plurality of control lines. The plurality of segments having one or more straight segments, one or more deflection segments, which are used to shape and steer the elongated member upon manipulation of at least one of the control lines. This causes the elongated member to deform into any desired shape capable of influencing the anatomical structure.

15 Claims, 9 Drawing Sheets

SYSTEM AND METHOD FOR INFLUENCING AN ANATOMICAL STRUCTURE

REFERENCE TO RELATED APPLICATIONS

This application is a continuation-in-part of U.S. patent application Ser. No. 11/283,104, filed on Nov. 18, 2005, now U.S. Pat. No. 7,621,908 the contents of which are incorporated herein by reference in their entirety.

FIELD OF THE INVENTION

This invention relates to a system for use in relocating or influencing anatomy; particularly, a system for use in tubular shaped anatomy; and more particularly to an assembly capable of laterally moving the esophagus during catheter ablation procedure.

BACKGROUND OF THE INVENTION

In an effort to ameliorate patient recovery time, many medical procedures are performed using minimally invasive techniques to access internal treatment sites. These smaller surgical fields generally require less surgical instrumentation, such as retractors, which are typically used to temporarily move neighboring tissue away from the treatment site during more invasive procedures. Obviously, this can have dire consequences if tissue proximally located to the treatment site is inadvertently damaged during surgery.

For example, one popular minimally invasive procedure to treat atrial fibrillation of the heart uses cardiac catheters through the femoral vein to the right atrium via the inferior vena cava. However, this treatment has increased risk of damaging the proximally located esophagus of the patient, in which the esophagus overlies the heart. Cardiac catheters are used to block or interfere with impulses radiating from ectopic foci inside the pulmonary veins that trigger atrial fibrillation. Electrophysiologists use cardiac catheters to ablate the heart tissue without the need for invasive open heart surgery, whereas Cardiovascular Surgeons open the chest wall to access the left atrium using an open chest procedure to effect a similar treatment. In this procedure, at least one catheter is inserted into the left atrium and is used to create a series of ablations or burns using an energy source, such as, radio-frequency (RF) energy, laser energy, ultrasound energy, cryogenics or the like. The ablations are formed around the os of the pulmonary vein and the left atrial wall of the heart. These ablations form scar tissue which does not conduct electrical impulses. Thus, the rapid and erratic impulses of atrial fibrillation are contained within the pulmonary veins by the wall of scar tissue that was formed by the ablation, and are prevented from reaching the atria and triggering it into an atrial fibrillation rhythm.

One of the most serious and, possibly fatal complications that may arise from the aforementioned procedure is an atrial-esophageal fistula (communicating hole in the posterior left atrial wall and adjacent esophagus) which is caused by thermal penetration of the walls of the atrium and esophagus by the ablation catheter. The esophagus is located at the center of the posterior mediastinum and is separated from the atrium only by the pericardial sac and/or a thin layer of fatty tissue and may be in contact with the atrium. The esophagus is supported at its upper end near the trachea and transits the diaphragm to connect with the stomach. The lower end of the esophagus is supported by the diaphragm. The thoracic portion of the esophagus between the trachea and the stomach is mobile and loosely restrained only by soft tissue, which allows the esophagus to move laterally in response to swallowing food, cardiac and lung movement, as well as upper body movements. The atrial-esophageal fistula may result, in part, from simple anatomy and the energy needed to develop ablations, as well as the design of the catheter electrode tip and other contributing factors, such as movement of the esophagus during the procedure. An atrial-esophageal fistula can lead to pericarditis (fluid between the outer wall of the heart and the pericardium) which restricts the heartbeat, causing hemorrhage, or other life threatening conditions, and sepsis which is caused by particulate matter passing from the esophagus into the left atrium and the circulatory system. When viewing these proposed ablation lesions, either pre-operatively or intra-operatively, the surgeon may be forced to change the location of some of the ablations because of the proximity to the esophagus. If a particular ablation(s) is considered necessary regardless of the location of the esophagus, the surgeon may be compelled to reduce the power to the electrode. Both of these options may result in suboptimal ablation lesions which may reduce the success rate of the procedure.

Therefore, what is needed in the art is a system and method for safely influencing and controlling the location of anatomical structure (e.g., organ) in relation to nearby tissue during a surgical procedure. In particular, the system could be used to control the location of the esophagus relative to the heart (e.g., atrium) during catheter ablation procedures.

SUMMARY OF THE INVENTION

The present invention is drawn toward a relocation system for influencing an anatomical structure. Specifically, the system includes an elongated member having a proximal and distal end and defined by a plurality of segments each having a superior and inferior surface. The plurality of segments are interconnected between the proximal and distal end by a plurality of control lines slidably disposed therethrough and attached to a terminal segment.

The plurality of segments include one or more straight segments, one or more deflection segments, and an abutting means located at the proximal end of the elongated member. The straight segments and deflection segments are constructed and arranged along the longitudinal axis of the elongated member to shape and steer it upon manipulation of at least one of the control lines by medical personnel.

Accordingly, it is a primary objective of the instant invention to provide a relocation system capable of moving and restraining an anatomical structure (esophagus, intestine, blood vessels, fallopian tube, or the like) away from the surgical site.

It is a further objective of the instant invention to provide a relocation system which can be used alone or in combination with a catheter (e.g., naso-gastric) to displace the catheter to an intermediate portion along its longitudinal axis.

It is yet another objective of the instant invention to include control lines made from at least one type of radiological material or having radiological markers thereon so that the surgeon is able to readily determine its location internally by fluoroscopy, as well as its orientation relative to the direction of planned relocation.

A further objective of the invention is to provide at least one or more of the plurality of segments made from at least one type of radiological material or having radiological markers thereon so that the surgeon may be able to readily determine their location internally by fluoroscopy.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure. Wherever possible, the same reference numbers will be used throughout the drawings to refer to the same or like parts.

Figure 1A:
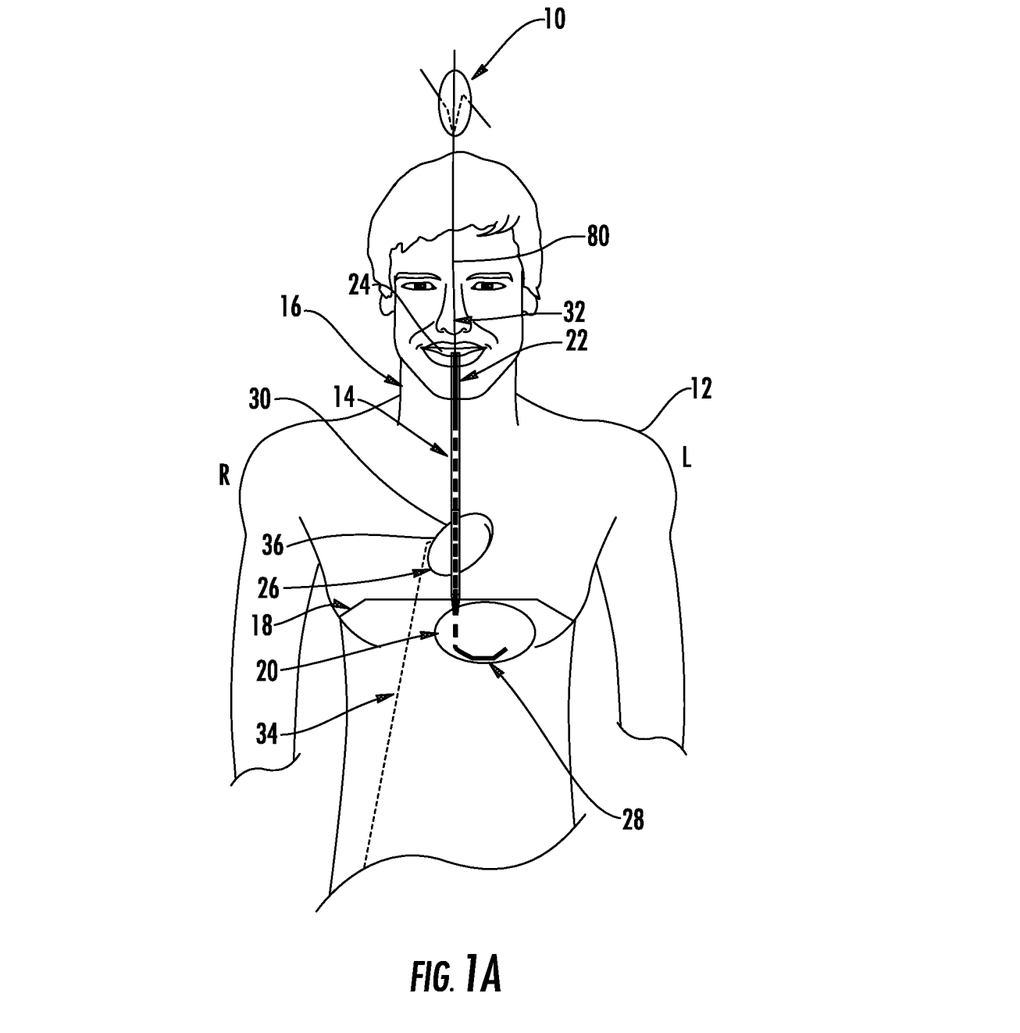
FIG. 1A is a representation of a supine patient with the present invention inserted through the patient's mouth, esophagus, diaphragm and into the stomach, with the esophagus residing behind the heart.
Figure 1B:
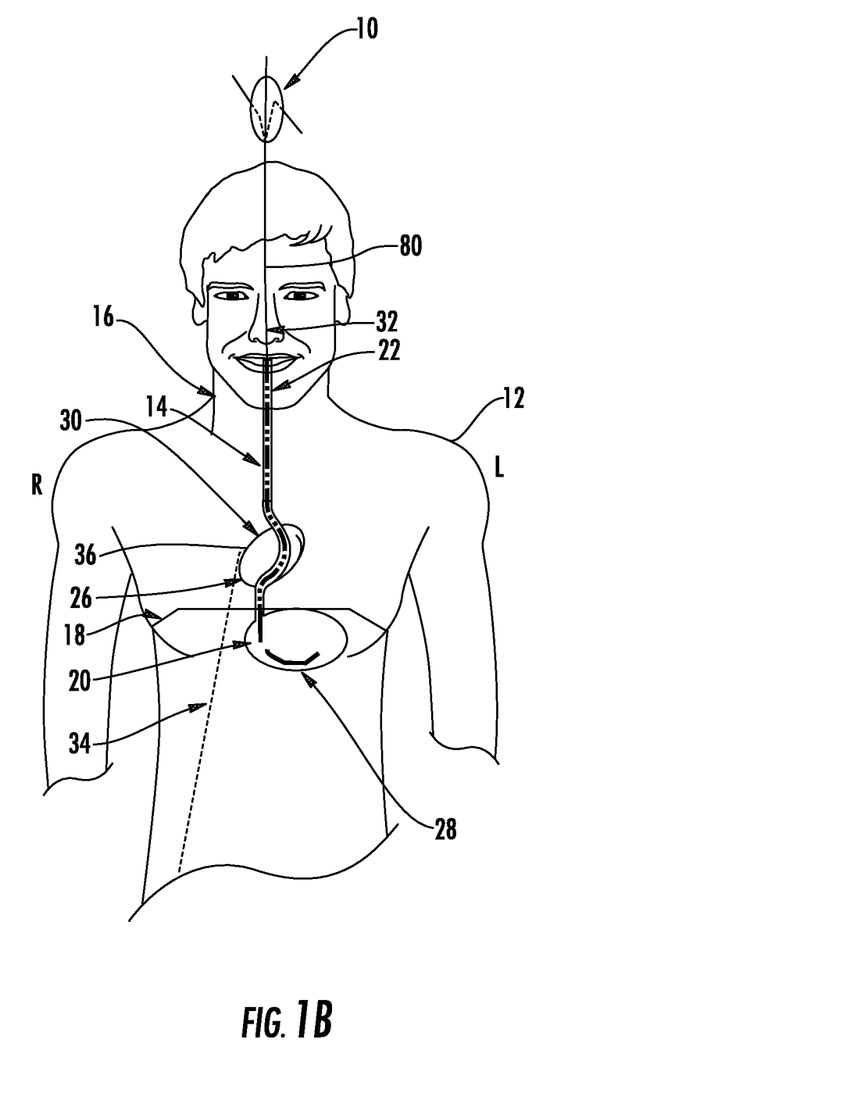
FIG. 1B is the same representation of FIG. 1A, in which the present inventive system has created a curve toward the left (L), thereby moving a portion of the esophagus away from behind a specific area of the heart.
Figure 2A:
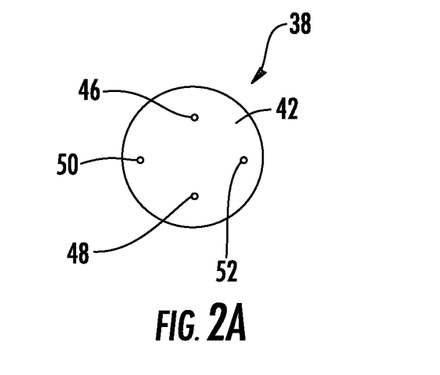
FIG. 2A illustrates the superior surface of a single straight segment as seen from the top.
Figure 2B:
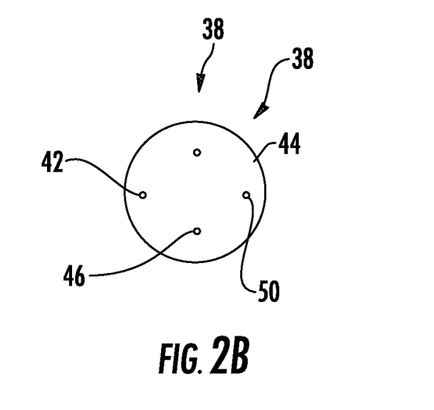
FIG. 2B illustrates the inferior surface of the straight segment of FIG. 2A as seen from the bottom.
Figure 2C:
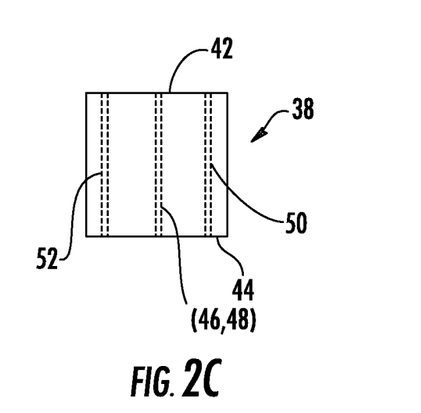
FIG. 2C illustrates an anterior view of the straight segment of FIG. 2A.
Figure 2D:
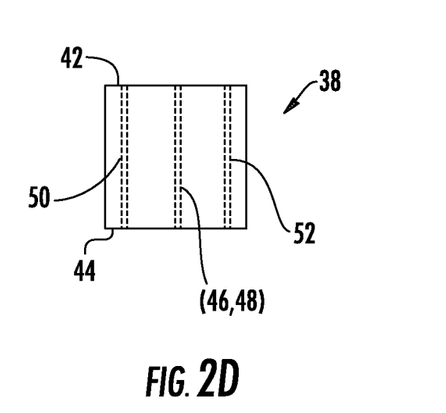
FIG. 2D illustrates a posterior view of the straight segment of FIG. 2A.
Figure 2E:
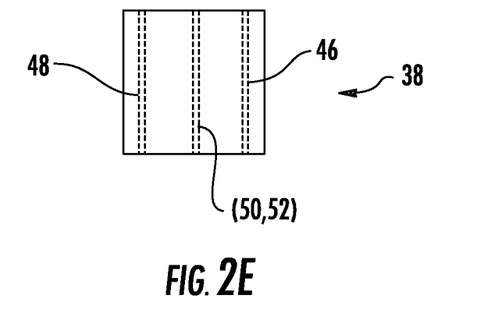
FIG. 2e illustrates a lateral view of the straight segment of FIG. 2A.
Figure 3A:
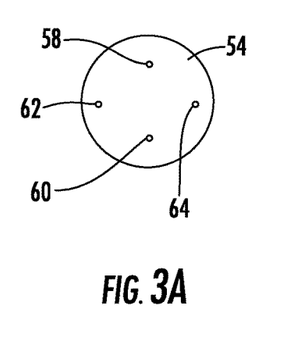
FIG. 3A illustrates the superior surface of a single deflection segment as seen from the top.
Figure 3B:
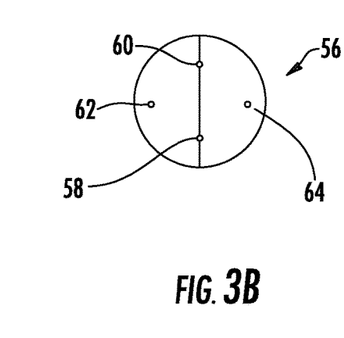
FIG. 3B illustrates the inferior surface of the deflection segment of FIG. 3A as seen from the bottom, illustrating the fulcrum formed by the beveled edges.
Figure 3C:
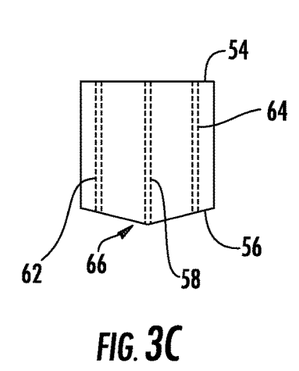
FIG. 3C illustrates an anterior view of the deflection segment of FIG. 3A of a segment with a beveled inferior surface.
Figure 3D:
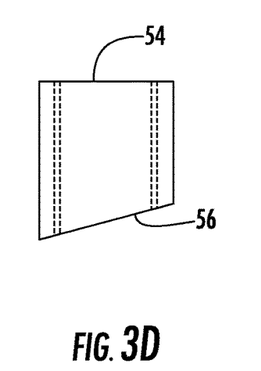
FIG. 3D illustrates the anterior view of a deflection segment which is angled on only one side.
Figure 4:
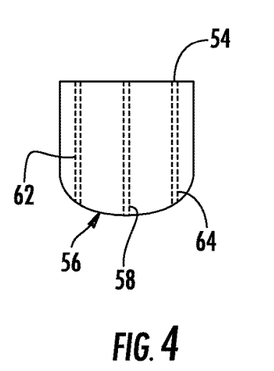
FIG. 4 illustrates the convex curved inferior surface of the deflection segment as seen from an anterior view in accordance with another embodiment.

FIGS. 1A-B illustrates an upper perspective view of the relocation system shown inside of a supine patient. By way of an overview, the system includes a control handle 10 located outside of the patient 12 and in physical communication with an elongated member 22 via at least one control line, described further below. The elongated member 22 is shown here with the proximal end 32 extending out of the patient's mouth 24 and longitudinally extending along the throat 16, esophagus 14 (which lies behind the heart 26 in FIG. 1A) passing through the diaphragm 18 with the distal end 28 disposed inside the stomach 20.

Referring now to FIG. 1B, the elongated member is shown having a curve toward the left formed along its longitudinal axis between the proximal and distal end upon manipulation of the control handle. The curved elongated member acts against the inner esophagus near the left atrium 30 so as to displace the esophagus away from behind the ablation site 36 on the heart. This is accomplished by unique construction of the elongated member, as explained below. It should be noted that the instant system produces movement consistent with the natural movement of the esophagus created during swallowing, breathing, etc., just at a determined time and direction.

The elongated member is comprised of a plurality of segments interconnected by at least one control line slidably disposed therethrough, see FIGS. 6-10E. As shown in the aforementioned FIGS., the plurality of segments include at least one or more straight segments 38 (FIGS. 2A-E) and one or more deflection segments 40 (FIGS. 3A-E). These straight and deflection segments may be arranged in any combination, order, or sequence to obtain the desired shape along the longitudinal axis of the elongated member.

Referring again to the embodiment shown in FIGS. 1A-B, the proximal end of the elongated member is formed from a series of straight segments placed in the superior esophagus, as well as a straight portion located in the distal esophagus where it passes through the diaphragm into the stomach. With these areas serving as proximal and distal anchors, the medial portion includes a combination of deflection and straight segments that can be moved laterally to create a curve along the longitudinal axis as the patient's anatomy permits. This enables the surgeon to manage the surgical field in a manner which reduces the possibility of damaging neighboring tissues. The ablation catheter path 34 is shown in FIGS. 1A-B proceeding from the right femoral vein to the atrium via the inferior vena cava, as is known in the art.

FIGS. 2A-E illustrate a single straight segment which includes a superior surface 42 (FIG. 2A) and inferior surface 44 (FIG. 2B) with channels disposed therebetween designed to slidably receive a control line therethrough. In accordance with a preferred embodiment there are four channels, a posterior axial control line channel 46, an anterior axial control line channel 48, a right deflection control line channel 52, and a left deflection control line channel 50.

Figure 5:
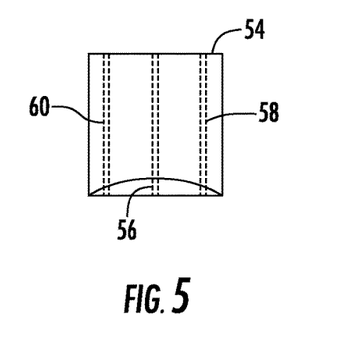
FIG. 5 illustrates the concave curved inferior surface of the deflection segment as seen from the side in accordance with yet another embodiment.

FIGS. 3A-E illustrate a single deflection segment which includes a superior surface 54 (FIG. 3A) and inferior surface 56 (FIG. 2B) with channels disposed therebetween designed to slidably receive a control line therethrough. Similar to the straight segments, the deflection segment include four channels, a posterior axial control line channel 58, an anterior axial control line channel 60, a right deflection control line channel 62, and a left deflection control line channel 64. As shown in FIGS. 3C-5, the inferior surface may be beveled to form a fulcrum 66 on which the segment pivot against, or have a convex curve (FIG. 4) or concave curve (FIG. 5). Although, the bevel and curves are shown only on the inferior surface 56, it is hereby contemplated that either or both the superior and inferior surfaces of the deflection segments may be curved or beveled. The straight and deflection segments are depicted herein with a cylindrical cross-sectional shape. However, at least one or all of the segments may have any cross-sectional shape deemed suitable, e.g., square, rectangular, oval, etc.

Figure 6:
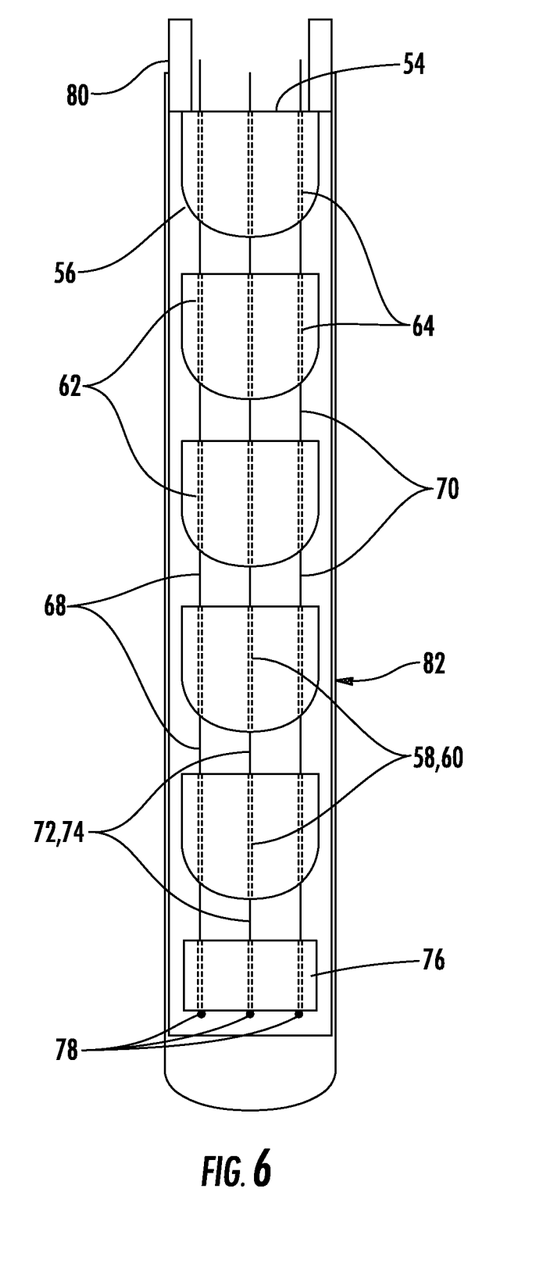
FIG. 6 illustrates an anterior view of the elongated member composed of a series of convex curved deflection segments before retraction of the axial or deflection control lines disposed therethrough.

Referring now to FIG. 6, which illustrates the proximal and distal portion of the elongated member showing a plurality of deflection segments in series and interconnected by a right deflection control line 68, an anterior/posterior axial control line 72, 74 (only one shown), and a left deflection control line 70. The elongated member is shown here before retraction of the axial or deflection control lines. As depicted in the figure, there is a terminal segment located at the distal end of the elongated member through which each of the control lines extend and attach at 78 (shown here simply knotted). The terminal end may be a deflection or straight segment. According to a preferred embodiment, the segments are surrounded by an outer sheath or coating 82 made from a flexible material (e.g., plastic, rubber, etc). The outer sheath may extend from the control handle to the distal tip of the device.

At the proximal end of the elongated member is an abutting means 80. The abutting means having sufficient rigidity to act against the superior surface of the most proximal segment to prevent the elongated member from retracting along its longitudinal axis when the control lines are retracted by the actuating means on the control handle, as discussed further below. According to a preferred embodiment, the abutting means is in the form of an inner sheath concentrically disposed within the outer sheath 82 and extends to the control handle (FIGS. 1A-B.)

Figure 7:
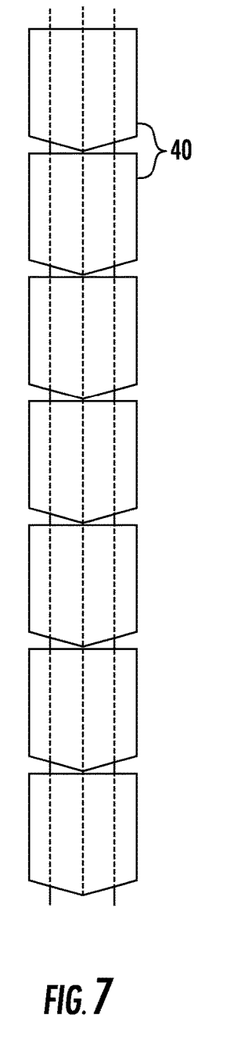
FIG. 7 illustrates an anterior view of a section of the elongated member composed of beveled deflection segments under retraction of the axial control lines.
Figures 8, 9:
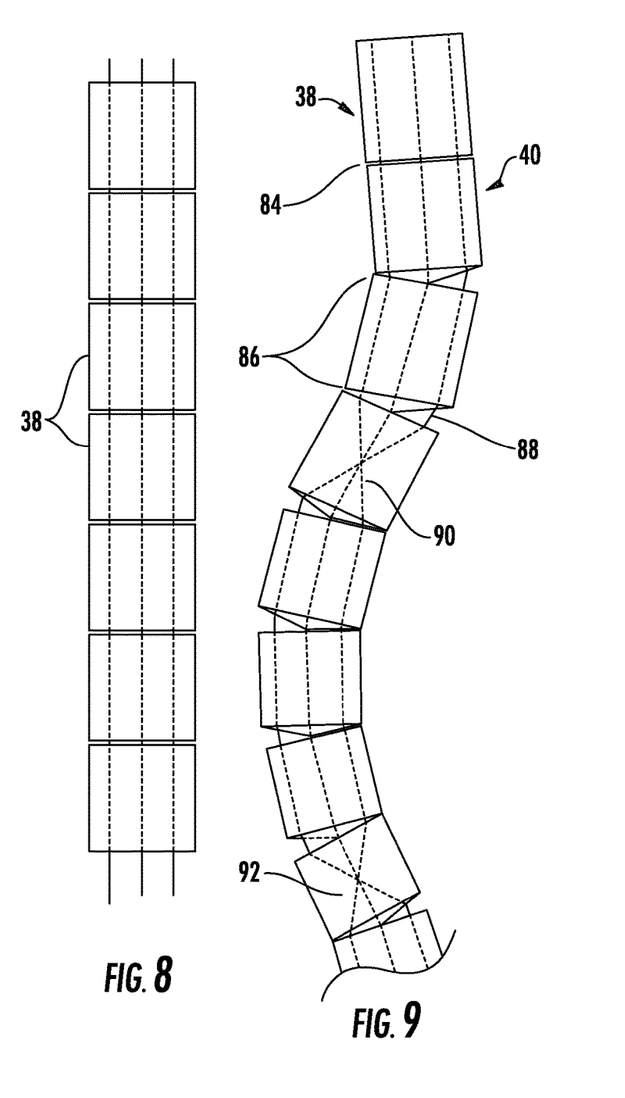
FIG. 8 illustrates an anterior view of a section of the elongated member composed of straight segments under retraction of the axial control line.
FIG. 9 illustrates a section of the elongated member composed of a series of both straight and deflection segments with the axial and right deflection line retracted to form a right curve along the longitudinal axis.

Referring now to FIGS. 7-8, each illustrates a section of deflection and straight segments, respectively. Each section is drawn together under tension by the plurality of control lines slidingly disposed therethrough and attached to a corresponding means to actuate each line (see FIGS. 11A-C). When the deflection segments are drawn together by the anterior and posterior axial control lines, the beveled or curved surface creates a surface against which the segments can pivot to create a curve along the longitudinal length of the elongated member, see FIG. 9. When the straight line segments are drawn together (FIG. 8), the linear superior and inferior surfaces create a stable and straight segment therealong.

FIG. 9, illustrates a section of the elongated member where the straight segments are interspersed with deflection segments and under tension to create a right sided bend or curve. This accomplished by increasing the tension on the anterior and posterior axial lines between adjacent straight segments which draw together their flat surfaces creating a rigid and straight section. The increased tension on the axial lines in the deflection segments draws the centers together, creating a fulcrum on which the surface can pivot to the right or left. The tension on the right deflection line draws the deflection edges together at point 86, resulting in a curve towards this side. A slack left deflection line allows the edges 88 on the relaxed side to separate, resulting in a curve toward the opposite side. By crossing the right deflection line over the left side, the direction of the curve is reversed at that segment 90. Similarly, by crossing the right deflection line back over the right side, the direction of the curve is again reversed at segment 92.

Figure 10A:
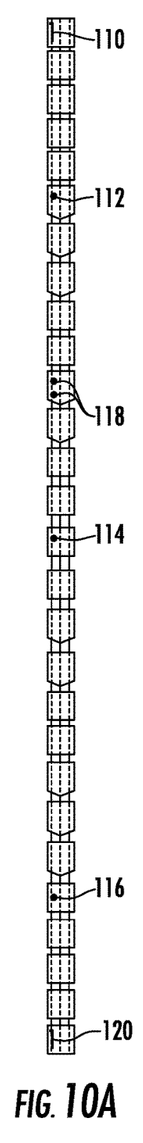
FIG. 10A illustrates a section of the elongate member composed of both straight and deflection segments without tension in the axial and deflection lines, which allows for flexibility during the insertion process.
Figure 10B:
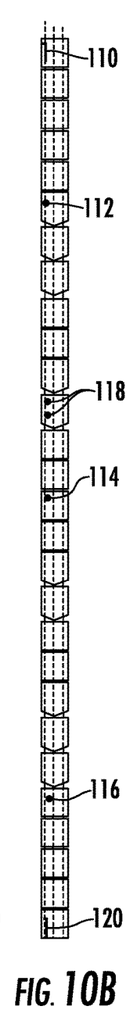
FIG. 10B illustrates a section of the elongate member composed of both straight and deflection segments with tension in the axial line(s)
Figure 10C:
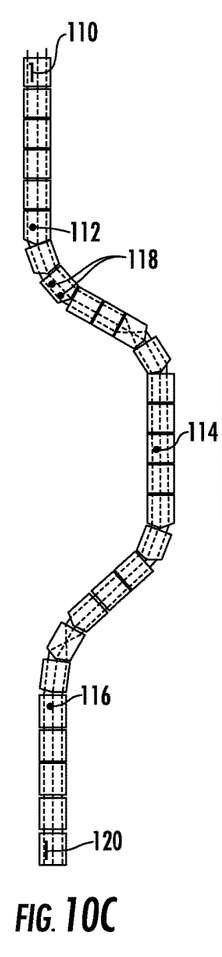
FIG. 10C illustrates a section of the elongated member composed of both straight and deflection segments configured to form a curve to the left along the longitudinal axis.
Figure 10D:
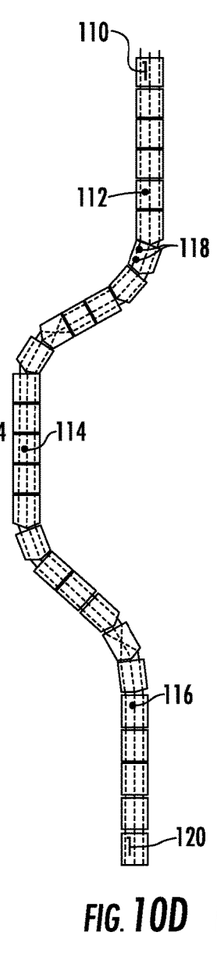
FIG. 10D illustrates a section of the elongated member composed of both straight and deflection segments configured to form a curve to the right along the longitudinal axis.
Figure 10E:
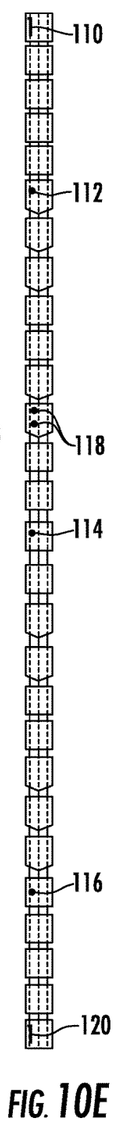
FIG. 10E again illustrates a section of the elongate member composed of both straight and deflection without tension in the axial and deflection lines, which allows for flexibility during the removal process.

FIGS. 10A-E, illustrate the steps from insertion to withdrawl of the inventive system. In FIG. 10A the elongated member is inserted without any tension in the control lines, thereby allowing flexibility between the segments for easy insertion into the patient. Next, tension in the axial lines is created to draw the segment together, as shown in FIG. 10B. To create the curve to the left (FIG. 10C), tension is placed on the left deflection lines and the right deflection lines are left slack. To create a curve to the right (FIG. 10D), tension is placed on the right deflection line and the left deflection line is allowed to become slack. Lastly, the elongated member is withdrawn after releasing tension from the axial and deflection lines, allowing movement to create space between the segments resulting again in flexibility for easy removal (FIG. 10E).

Figures 11A, 11B, 11C, 12A, 12B:
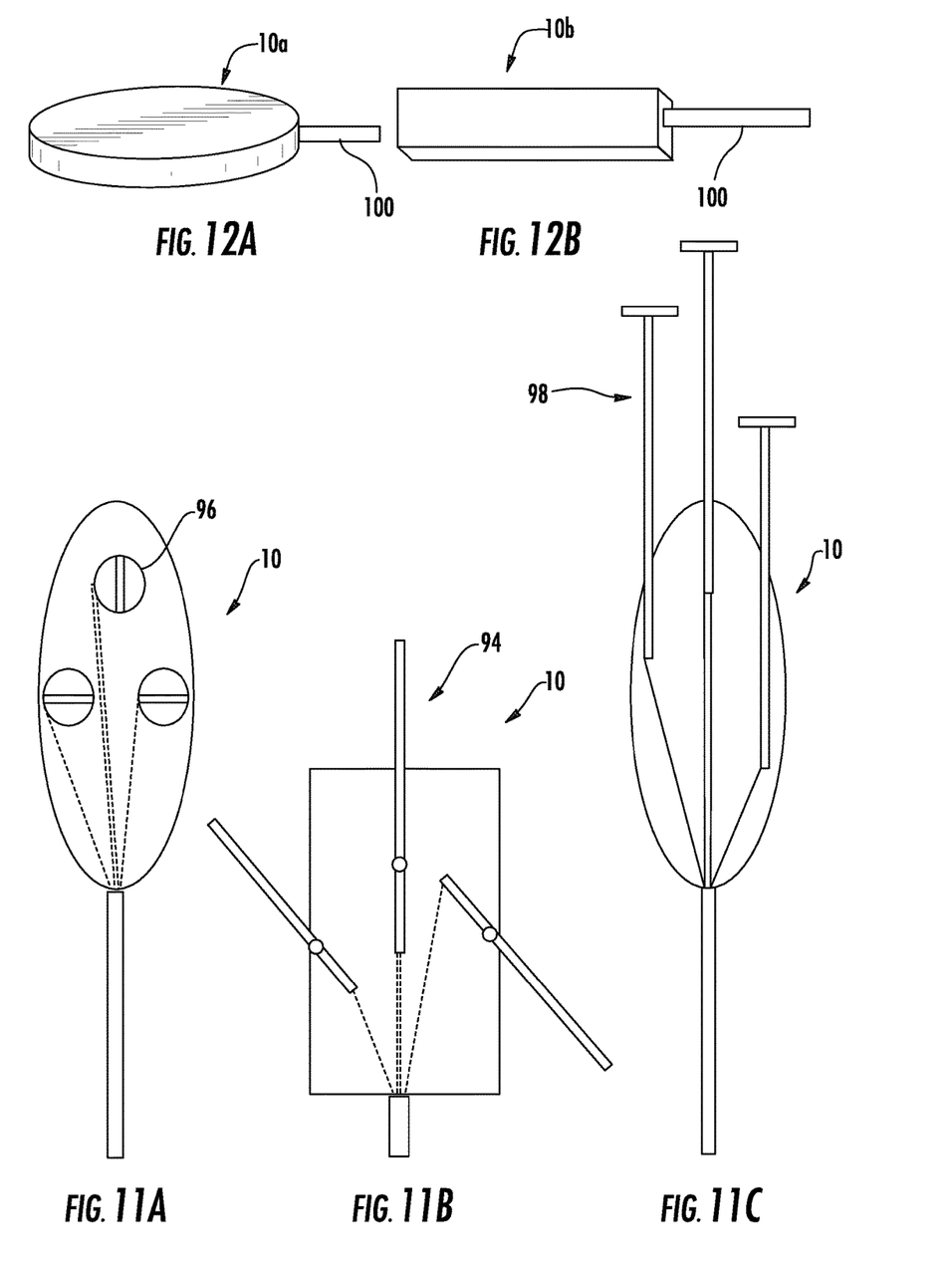
FIG. 11A illustrates one embodiment of a control handle including a spool type means to actuate each of the control lines.
FIG. 11B illustrates another embodiment of a control handle including a lever type means to actuate each of the control lines.
FIG. 11C illustrates one embodiment of a control handle including a piston type means to actuate each of the control lines.
FIG. 12A illustrates a control handle having an oval handle body.
FIG. 12B illustrates a control handle having a rectangular handle body.

As shown in the various embodiments in FIG. 11-C, the control handle includes a means to actuate each of the plurality of control line independently. Although shown here as pivoting levers 94 in FIGS. 1A-B and FIG. 11B, other means for actuating the control lines are contemplated herein. For example, spool mechanisms 96 (FIG. 11A) or piston 98 (FIG. 11c) mechanisms may be used so long as the mechanism is able to create and hold tension on the control lines. In addition, the handle may be any shape deemed suitable. For example, FIG. 12A illustrates an oval handle 10a and FIG. 12b illustrates a rectangular handle 10b each include flexible tube 100 or outer sheath 82 constructed and arranged to house the control lines which lead to the plurality of segments.

Figure 13A:
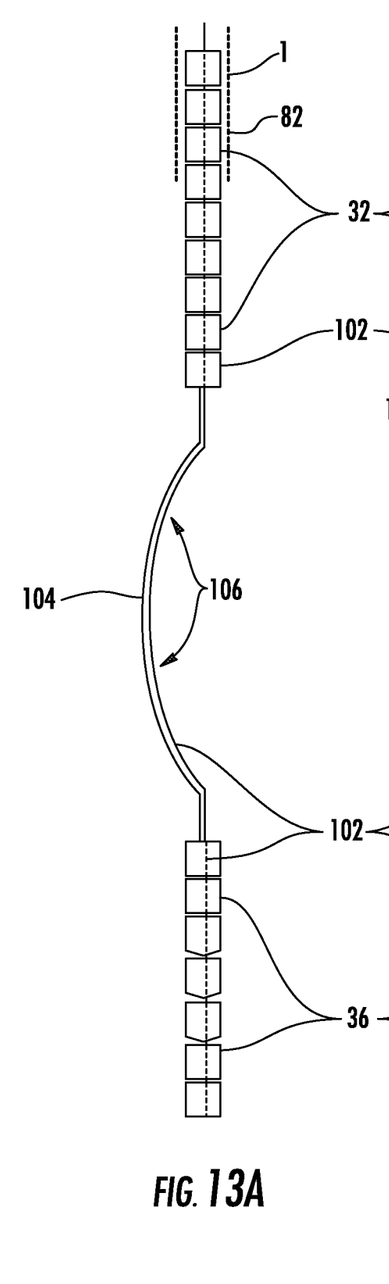
FIG. 13A illustrates an anterior view of a portion of the elongate member in accordance with another embodiment.
Figure 13B:
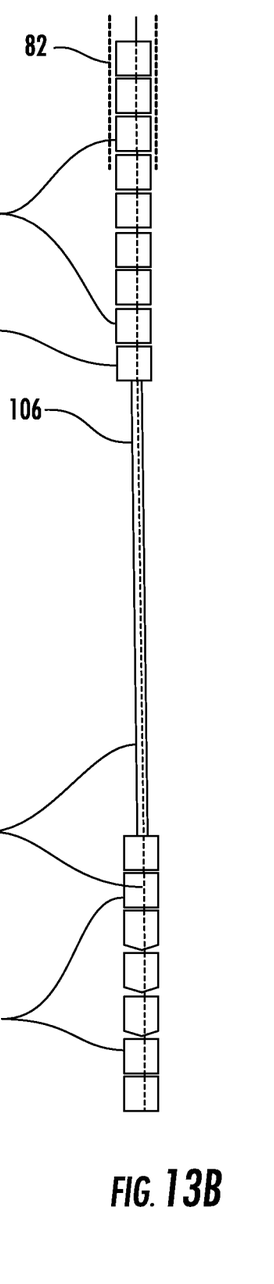
FIG. 13B illustrates a lateral view of a portion the elongate member of FIG. 13A.

Referring to another embodiment of the invention shown in FIGS. 13a-b, which may also be used to laterally move anatomy away from a surgical site. For example, this system may also be used to fix the displaced portion of the esophagus safely beyond the area of thermal lesions. A first control wire 102 is slidably disposed throughout the plurality of segments through a corresponding channel and controlled at the control handle in a manner similar to the axial and deflection lines as described above. A second control wire 104 does not extend through the plurality of segments, rather it is attached to the inferior and superior surfaces of the proximal and distal segments, 32, 36, as shown in FIG. 13a,b. The second control wire 104 is used in conjunction with the first control wire 102 to produce a curve 106 (FIG. 13a) or, independently, to form the elongated member in other shapes. Continuing with the esophagus example, the plurality of segments are placed in position within the esophagus and the first control wire is pulled until it acts against the proximal segments, applying longitudinal pressure to the second control wire causing it to bend and displace the elongated member and esophagus away from the ablation lesions laterally and posteriorly as the patient's anatomy permits. As shown in FIG. 13a, the curvature of the elongated member is right lateral however, the control wires may be manipulated to force the anatomy in any direction. As with the previous embodiment, the system of this embodiment may be enclosed throughout its longitudinal length by a flexible outer sheath 82.

As shown here in FIG. 13a, the first control wire is round and the second is flat. However, the control wires may be round, flattened, single strand or multi-strand, such as a guide wire. Also, control wires made from shape retaining memory materials, such as Nitinol, can be used. These wires are pre-formed at a certain temperature with the desired curve and then cooled and straightened. When the elongated member is placed in the body, the wires assume their original curved shape as they become heated.

According to preferred embodiment, the axial control lines (posterior, anterior) and deflection control lines may be made from any durable material deemed suitable, such as polymeric, metal, natural fiber, or combinations thereof. In addition, one or more of these control lines and/or control wires (first, second) may include radiologic material or markers capable of being visualized by fluoroscopy to improve visualization of the location of the elongated member inside the patient's body. For example, the two axial lines can be made of wire, which can be visualized by fluoroscopy. If the two wires are lined up, or on top of each other, when viewed in the anterior and posterior orientation the surgeon will know the deflection curve will be created on a lateral plane. If the wires are not lined up, the elongated member can be rotated until they are in a correct anterior/posterior orientation.

Similarly, at least one or more of the plurality of segments may include at least different identifying markers or types of radiologic material (numbers, dots, etc.) which allows the surgeon to readily determine the location of various parts (e.g., proximal end, distal end) of the elongate member by fluoroscopy or the like. For example, as shown in FIGS. 10A-E, a radio-opaque bar 110 marks the proximal end of the member and the 120 marks the distal end of the elongate member, a single round radio-opaque marker identifies the beginning, midpoint and end of the deflection, (112, 114, 116) and a double marker 118 is aligned with the mid-atrium during insertion. It can be used to indicate the midpoint of the impending deflection.

All of the aforementioned embodiments of the inventive system is not restricted for use in the esophagus. The present invention may be used for moving and restraining any anatomy (intestine, blood vessels, fallopian tubes, etc.) away from certain areas overlying or proximate to the surgical site. Moreover, the system can used in other species (humans, canine, equine, etc.)

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A relocation system for influencing an anatomical structure, said system comprising:
an elongated member traversable between a non-actuated position and an actuated position, said elongated member having a proximal and distal end, said elongated member defined by a plurality of individual segments each having a superior and inferior surface, each individual segment of said plurality of individual segments is completely separated from an adjacent individual segment positioned above or below by a space when in a non-actuated position, said plurality of individual segments interconnected between said proximal and distal end by a plurality of control lines slidably disposed therethrough and secured to a terminal segment, said plurality of control lines comprising at least one posterior or anterior axial control line positioned through the middle portion of said plurality of individual segments and configured to draw adjacent individual segments together and a pair of deflection control lines, said pair of deflection control lines comprising a first deflection control line positioned to the left of said at least one posterior or anterior axial control line and a second deflection control line positioned to the right of said at least one posterior or anterior axial control line, said pair of deflection control lines configured to cause at least one individual segment to move left or right relative to an adjacent individual segment when drawn together, said elongated member having at least one individual segment having said first deflection control line crossing over from said left side to said right side of said at least one posterior or anterior axial control line and extending to said right side of at least one adjacent individual segment, and at least one individual segment where said first deflection line positioned on said right side of said at least one posterior or anterior axial control line crosses back from said right side to said left side of said at least one posterior or anterior axial control line and extends to said left side of at least one adjacent individual segment;

said elongated member further comprising at least one individual segment of said plurality of individual segments having said second deflection control line crossing over from said right side to said left side of said at least one posterior or anterior axial control line and extending to said left side of at least one adjacent individual segment, and at least one individual segment having said second deflection control line positioned on said left side of said at least one posterior or anterior axial control line crossing back from said left side to said right side of said at least one posterior or anterior axial control line and extending to said right side of said at least one adjacent individual segment;

said plurality of segments having one or more straight segments, one or more deflection segments, and an abutting member located at the proximal end of said elongated member, said superior surface or said inferior surface of said straight segments configured to provide a straight segment when in contact with an adjacent segment, thereby resulting in at least a portion of said elongated member forming a straight portion, and said deflection segments being constructed and arranged along said longitudinal axis to shape and steer said elongated member upon manipulation of at least one of said control lines, at least one of said superior or inferior surfaces of said deflection segments has a shape effective to cause an adjacent deflection segment to move left or right along the longitudinal axis thereof when in contact, thereby resulting in said elongated member forming a shaped curve via actuation of said one or more control lines, said shape creating a fulcrum at the central longitudinal axis of said elongated member to create a curve along the longitudinal axis thereof;

whereby manipulation of at least one of said control lines causes said elongated member to reconfigure into a desired shape along a single plane wherein at least one segment is in a parallel axis to at least one other segment.

2. The relocation system of claim 1, wherein at least one of said superior or inferior surfaces of said deflection segments is angled to create said fulcrum at the central longitudinal axis of said elongated member to create a curve along the longitudinal axis thereof.

3. The relocation system of claim 1, wherein said control lines include a posterior axial control line, an anterior axial control line, a first deflection control line, and a second deflection control line each slidably disposed within a corresponding channel.

4. The relocation system of claim 3, further comprising a control handle configured to independently actuate each of said plurality of control lines.

5. The relocation system of claim 3, wherein said posterior axial control line and said anterior axial control line includes radiologic material capable of being visualized by fluoroscopy.

6. The relocation system of claim 1, further comprising a control handle configured to actuate each of said plurality of control lines.

7. The relocation system of claim 1, wherein said elongated member is encapsulated by a protective outer flexible sheath.

8. The relocation system of claim 1, wherein at least one of said plurality of segments includes radiologic material capable of being visualized by fluoroscopy.

9. The relocation system of claim 1, wherein at least one proximally located segment and at least one distally located segment includes a first radiologic material capable of being visualized by fluoroscopy.

10. The relocation system of claim 9, wherein at least one medially located segment includes a second radiologic material capable of being visualized by fluoroscopy.

11. The relocation system of claim 1, wherein at least one of said plurality of control lines includes radiologic material capable of being visualized by fluoroscopy.

12. The relocation system of claim 1, further comprising at least one flexible control wire located intermediate between said plurality of segments, said at least one flexible control wire constructed and arranged to be reversibly deformed between a curved state and substantially linear state along said longitudinal axis of said elongated member.

13. A steerable and shapeable catheter adapted for repositioning an internal anatomical structure, comprising:
  a flexible outer sheath having a proximal end and a distal end;
  a plurality of individual segments serially arranged within said flexible outer sheath between said proximal and distal end thereof and movable independent of adjacent segments about a plurality of control lines when in a non-actuated position, each of said plurality of individual segments is completely separated and spaced apart from said adjacent individual segment positioned above or below in said non-actuated position, said plurality of individual segments including one or more straight segments, one or more deflection segments having a shape effective to cause said outer sheath to bend along a longitudinal axis thereof forming a shaped curve via actuation of one or more of said plurality of control lines, said shape creating a fulcrum at a central longitudinal axis to create a curve along the longitudinal axis thereof, and at least one terminal segment;
  each of said segments having a superior surface and an inferior surface, said segments further including a plurality of channels, each of said plurality of channels being constructed and arranged for passage of at least one control line therethrough between said superior and inferior surfaces, said plurality of segments being arranged about at least one control line to form a plurality of bends in a single plane via actuation of one or more control lines, said segments traversable via actuation of at least one control line between a first position having each of said plurality of segments having a space between adjacent segments when said at least one control line is not under a tension, and a second position having at least one of said superior or inferior surface of one segment contacting at least one of said superior or inferior surface of an adjacent segment when at least one of said plurality of said control lines is actuated;

said plurality of control lines constructed and arranged to enable manipulation of said catheter along a particular path and shape wherein at least one segment is in a parallel axis to at least one other segment, said plurality of control lines comprising at least one posterior or anterior axial control line configured to draw adjacent individual segments together and a pair of deflection control lines, said pair of deflection control lines comprising a first deflection control line positioned to the left of said at least one posterior or anterior axial control line, and a second deflection control line positioned to the right of said at least one posterior or anterior axial control line, said pair of deflection control lines configured to cause at least one individual segment to move left or right relative to an adjacent individual segment when drawn together, at least one individual segment having crossed first and second deflection control lines, wherein said first deflection control line is positioned to the right of said posterior or axial control line in one or more individual segments proceeding said individual segment having said crossed deflection lines, and said second deflection control line is positioned to the left of said posterior or axial control line in one or more individual segments proceeding said individual segment having said crossed deflection lines, and at least one second individual segment wherein said first deflection control line positioned to the right of said posterior or axial control line in one or more individual segments is crossed back to be positioned to the left of said at least one posterior or axial control line in one or more proceeding adjacent individual segments, and said second control line positioned to the left side of said posterior or axial control line in one or more individual segments is crossed back to be positioned to the right of said at least one posterior or axial control line in one or more proceeding adjacent individual segments;

an abutting member positioned within said flexible outer sheath at said proximal end thereof for abutting against said plurality of segments to prevent retraction thereof; and a control handle, positioned at said proximal end of said catheter and in communication with each of said control lines;

whereby manipulation of said control handle enables simultaneous steering, traversal, and shaping of said catheter within said anatomical structure.

14. The relocation system of claim 1, wherein said plurality of control lines are made from nitinol.

15. The steerable and shapeable catheter of claim 13 wherein said plurality of control lines are made from nitinol.

* * * * *